United States Patent [19]

Ueno et al.

[11] Patent Number: 4,647,458

[45] Date of Patent: Mar. 3, 1987

[54] LIQUID BACTERICIDE FOR FOODS AND FOOD PROCESSING MACHINES OR UTENSILS, EMPLOYING A SYNERGISTIC MIXTURE OF ETHYL ALCOHOL, AN ORGANIC ACID AND PHOSPHORIC ACID

[75] Inventors: Ryuzo Ueno, Nishinomiya; Tatsuo Kanayama, Takarazuka; Yatsuka Fujita; Munemitsu Yamamoto, both of Nishinomiya, all of Japan

[73] Assignee: Kabushiki Kaisha Ueno Seiyaku Oyo Kenkyujo, Osaka, Japan

[21] Appl. No.: 581,366

[22] Filed: Feb. 14, 1984

Related U.S. Application Data

[63] Continuation-in-part of Ser. No. 305,845, Sep. 25, 1981, abandoned.

[51] Int. Cl.$^4$ .............................................. A01N 59/26

[52] U.S. Cl. ....................................... 424/128; 422/28

[58] Field of Search ......................................... 424/128

[56] References Cited

U.S. PATENT DOCUMENTS

| | | | |
|---|---|---|---|
| 146,781 | 1/1874 | Reynoso | 424/128 |
| 2,118,566 | 5/1938 | Wayne | 424/128 |
| 3,697,651 | 10/1972 | Khan et al. | 424/128 |

OTHER PUBLICATIONS

Schumbury; C.A., vol. 6 (1912) p. 1167.

*Primary Examiner*—Allen J. Robinson
*Attorney, Agent, or Firm*—Wenderoth, Lind & Ponack

[57] ABSTRACT

A liquid bactericide for foods and food processing machines or utensils, said bactericide comprising as active ingredients 98.0 to 2.3% (W/V) of ethyl alcohol, 1.0 to 96.7% (W/V) of an organic acid selected from the group consisting of lactic acid, acetic acid, citric acid, tartaric acid, gluconic acid, malic acid, ascorbic acid and phytic acid and 1.0 to 96.7% (W/V) of phosphoric acid; said bactericide being capable of sterilizing within 30 seconds when used in an aqueous solution, such that the concentration of active ingredients in solution consists of 14 to 1% (W/V) of ethyl alcohol, 13.0 to 0.3% (W/V) of said organic acid and 0.7 to 0.03% (W/V) of phosphoric acid.

7 Claims, No Drawings

LIQUID BACTERICIDE FOR FOODS AND FOOD PROCESSING MACHINES OR UTENSILS, EMPLOYING A SYNERGISTIC MIXTURE OF ETHYL ALCOHOL, AN ORGANIC ACID AND PHOSPHORIC ACID

This application is a continuation-in-part application of U.S. Ser. No. 305,845 filed on Sept. 25, 1981, now abandoned.

This invention relates to an effective and safe liquid bactericide for foods and food processing machines or utensils, said bactericide comprising a combination of (1) ethyl alcohol and (2) an organic acid or its salt and/or an inorganic acid or its salt, especially, comprising a combination of (1) ethyl alcohol, (2) an organic acid and (3) phosphoric acid, and a method for killing noxious bacteria which adhere to foods and food processing machines or utensils to cause food poisoning or spoilage.

Nowadays, a variety of foods are processed in great quantities at fixed places and transported from there to places of consumption. Accordingly, a long period of time elapses during transportation of the processed foods from the manufactures to the consumers, and also until the consumers cook or eat them. During this time, various problems tend to arise. The greatest problem is the occurrence of food poisoning and spoilage owing to infecting microorganisms, and a great deal of efforts have been made to prevent it.

Food poisoning and spoilage are caused mainly by bacterial infection of raw materials, and bacterial infection during processing and distribution. In this regard, it is generally thought that seafood pastes, and hams and sausages have a high degree of safety because they undergo heat-treatment during processing. These foods, however, are susceptible to secondary contamination during a time period between the heat-treatment and packaging. In order to prevent food poisoning and spoilage of these foods, it is necessary to prevent secondary contamination.

Salads, Chinese foods, hambergs, meat balls, etc. are among those processed foods which have recently shown a great demand in the Japanese market, and the demand for salads containing raw vegetables is especially high. It is known however that raw vegetables used for salads, such as cucumbers, tomatoes, cabbage, Chinese cabbage, onions and celery, are frequently contaminated strongly by food-poisoning bacteria and spoiling bacteria. Presently, the noxious bacteria infecting vegetables is controlled by the blanching method. This method, however, has a defect in that it involves immersing the vegetables in a liquid kept at a high temperature which results in the tissues of the vegetables being destroyed by heat, and their flavor markedly decreased. Investigations have been undertaken, on the other hand, to remove the contaminating bacteria by an immersion or spraying technique using sodium hypochlorite, acetic acid, etc. However, since the chemicals must be used in high concentrations, they are likely to cause offensive odors, and adversely affect the flavor of foods and the health of the consumers.

Contamination of the human body (e.g., working personnel and cooks in food processing factories), seafoods, chickens (especially boilers), and chicken eggs by food-poisoning bacteria also poses a problem. For removal of these bacteria, it is the general practice to treat them with an aqueous solution of sodium hypochlorite in a concentration of less than 200 ppm (as available C1), but the effect of this treatment is not sufficient. If the sodium hypochlorite is used in a concentration of 200 ppm or more, its odor remains in the chicken flesh, for example, and its flavor is drastically impaired.

Hydrogen peroxide has high bactericidal activity with little deleterious effects on foods when used in effective concentrations. However, since its carcinogenicity was discovered, it cannot be used in food treatment. It is well known on the other hand that ethyl alcohol has been used widely as medical disinfectant because of its high safety and strong antimicrobial activity. In some food processing plants, investigations are being made to utilize the bactericidal activity of ethyl alcohol, and to eliminate food-poisoning and to destroy bacteria which spoils the foods and increase their preserving effects by directly spraying ethyl alcohol to the foods or directly dipping them in ethyl alcohol.

In order to obtain a sufficient effect from ethyl alcohol alone, the concentration of ethyl alcohol should be at least 70%. Such a high ethyl alcohol concentration results in a strong shell of ethyl alcohol and markedly impairs the flavor of foods. Or it degenerates proteins to reduce the quality of foods and their discoloration. Inorganic acids such as phosphoric acid have a strong sterilizing effect, but for a sufficient effect, they have to be used in a concentration of more than 30%. At effective concentrations, the irritation and sour taste inherent to phosphoric acid remains in the food thereby reducing the palatability of the foods. Organic acids, such as lactic acid or acetic acid, also exhibit a sterilizing effect in high concentrations. In this case, too, their inherent irritating odors and sour tastes greatly impair the flavor of foods. The high-concentration ethyl alcohol, inorganic acids and organic acids are unsuitable as bactericides for foods processing machines because they also adversely affect the working environment by their inherent irritating odors.

In the light of these circumstances, no effective means has been yet established for the removal and kiling of noxious microorganisms adhering to foods, food processing machines or utensils etc., despite its utmost importance in food sanitation and food processing.

It is an object of this invention therefore to provide a bactericide for foods and food processing machines or utensils, which does not deteriorate the flavor, and quality of foods nor destroy the food processing environment, and has very low toxicity and high safety.

The present inventors have now found that an excellent synergistic bactericidal effect can be obtained by using a mixture of ethyl alcohol and at least one material selected from organic acids, inorganic acids and salts thereof, and contaminating bacteria can be destroyed at much lower concentrations than in the case of using the individual components of the mixtures.

Thus, according to this invention, there is provided a liquid bactericide for foods and food processing machines or utensils, comprising as active ingredients (1) ethyl alcohol and (2) an organic acid or its salt and/or an inorganic acid or its salt.

Examples of the organic acids used in this invention and their salts include lactic acid, acetic acid, tartaric acid, gluconic acid, citric acid, ascorbic acid, malic acid, succinic acid, fumaric acid, and phytic acid and salts thereof. Examples of the inorganic acids and their salts, on the other hand, include phosphoric acid, condensed phosphoric acids (e.g., acidic pyrophosphoric acid, hexametaphosphoric acid, ultraphosphoric acid, etc.), nitric acid, sulfuric acid, and hydrochloric acid, and their salts.

Generally, the bactericide of this invention preferably consists of 99.9 to 2.0% (W/V) of ethyl alcohol and 0.1 to 98.0% (W/V) of at least one acid or acid salt, although it varies depending upon the types of the acids and salts used. In addition to these active ingredients, the bactericide of the invention may contain small amounts of water and a polyhydric alcohol such as propylene glycol and glycerol. When the acid or its salt is not easily soluble in ethyl alcohol, the addition of a small amount of water is preferred in order to obtain a uniform liquid bactericide.

The bactericide of this invention is usually used as a solution in water. Despite the fact that the bactericide of the invention contains the active ingredients in very low concentrations, it shows better bactericidal effects than the individual ingredients used separately. This synergistic effect can be seen from Experimental examples and Examples given hereinbelow. For example, the concentrations of ethyl alcohol and the acid or its salt required for performing sterilization within 30 seconds using an aqueous solution can be decreased to 0.5 to 35% (W/V), and 0.005 to 20% (W/V), respectively.

The pH of the aqueous solution of the bactericide of the invention is preferably not more than 4.0.

When the bactericide of the invention consists of ethyl alcohol and at least one organic acid or salt, it preferably contains 99.4 to 20% (W/V) of ethyl alcohol and 0.6 to 80% (W/V) of the organic acid or its salt. Usually, this bactericide is used in the form of an aqueous solution in which the concentration of ethyl alcohol is 35 to 5%, preferably 10 to 5%, (W/V) and the concentration of the organic acid or its salt is 20 to 0.5%, preferably 10 to 1% (W/V).

When the bactericidal agent of this invention consists of ethyl alcohol and at least one inorganic acid or salt, it preferably contains 99.9 to 20% (W/V) of ethyl alcohol and 0.1 to 80% (W/V) of the inorganic acid or its salt. Usually, this bactericide is used in the form of an aqueous solution in which the concentration of ethyl alcohol is 35 to 5%, preferably 10 to 5% (W/V) and the concentration of the inorganic acid or its salt is 0.005 to 20%, preferably 0.005 to 10%, (W/V).

When the bactericide of the invention consists of ethyl alcohol, at least one organic acid or salt and at least one inorganic acid or salt, the bactericide preferably contaings 98.0% to 2.3% (W/V), 96.7 to 1.0% (W/V) of the organic acid or its salt, and 96.7 to 1.0% (W/V) of the inorganic acid or its salt. Usually, this bactericide is used in the form of an aqueous solution in which the concentration of ethyl alcohol is 18.6 to 1%, preferably 14 to 1%, (W/V), the concentration of the organic acid or its salt is 31 to 0.3%, preferably 13.0 to 0.3%, (W/V), and the concentration of the inorganic acid or its salt is 10 to 0.03%, preferably 0.7 to 0.03%, (W/V).

The proportions and the effective concentrations of these components in these bactericides mentioned above are only examples which can effect sterilization within 30 seconds. They can be properly changed depending upon the type of foods to be sterilized, the contact time, the contacting method, etc.

For sterilization, an aqueous solution of the bactericide of the invention is contacted with a food or food processing machine or utensil.

Examples of foods which can be sterilized suitably by the method of this invention include seafood and meat products (such as fish pastes, sausage, ham, and bacon), vegetables, especially those eaten raw (such as cucumbers, tomatoes, cabbage, onions, lettuce and celery), various types of noodles, spaghetti, macaroni, seafoods, meat, chicken, chicken eggs, and semi-dried or dried products of seafoods and meats.

Examples of the food processing machines and utensils include cooking plates, cooking knives, food cotainers, cleaning cloths, and various devices used in food processing plants such as agitators, mixers, homogenizers, automatic cutters, conveying containers and packing containers.

Contacting of foods or food processing machines and utensils with the bactericide can be effected, for example, by dipping, spraying wiping, etc.

Since the bactericide of the invention has a high bactericidal activity at low concentrations, sterilization can generally be achieved by effecting the contacting for less than 30 seconds. Longer contacting does not appreciably reduce the flavor and quality of foods, nor give rise to any safety problems. Noxious bacteria adhering to the working personnel and cooks can be destroyed when they dip their hands in an aqueous solution of the bactericide of the invention, or wipe their hands with an absorbent cotton or gauze impregnated with the bactericide solution.

The use of the bactericide of the invention in this manner prevents food poisoning and increases the preservability of processed foods by inhibiting their spoilage for a prolonged period of time.

The following Experimental Examples and Examples illustrate the present invention more specifically.

In Experimental Examples 1 to 3, effective combinations of bactericidal components were determined in vitro using *Escherichia coli* (NIHJ-JC-2) which is a food-poisoning bacterium regarded as the most important contamination-indicating bacterium in food sanitation.

In Examples 1 to 7, bactericidal compositions prepared on the basis of the results of Experimental Examples 1 to 3 were used for foods and food materials to determine their bactericidal and bacteria-removing effects.

All percentages in these examples are by (W/V)%.

EXPERIMENTAL EXAMPLE 1

(A) The following experiment was conducted in order to examine the bactericidal effects of a mixture of ethyl alcohol and an inorganic acid substance.

*Escherichia coli* (NIHJ-JC-2) was inoculated in a brain heart infusion broth (BHI), and cultivated at 37° C. for 24 hours. The culture broth was diluted to 1/19 with sterilized physiological saline. The resulting *Escherichia coli* suspension was used as a sample. Phosphoric acid, acidic sodium pyrophosphate, sodium hexametaphosphate, sodium ultraphosphate and nitric acid were used as inorganic acid substances.

One milliliter of the sample bacterial suspension was added to 9 ml of a test chemical solution prepared by adding physiological saline in ethyl alcohol and each of the inorganic acid substances so that the concentration of these compounds reached 10/9 of the concentrations indicated in Table 1. They were immediately mixed, and maintained at 20° C. After a contact time of 30 seconds, one platinum loopful of the mixture was inoculated in a fresh BHI broth, and cultivated at 37° C. for 48 hours. Growth of the bacterium in the culture broth was observed with the naked eyes. When no growth of the bacterium was noted, the result was evaluated as (−) which means that complete sterilization was possible, and when growth of the bacterium was noted, the result was evaluated as (+) which means that sterilization was impossible. The concentrations of the chemicals which were required for complete sterilization were measured. The results are shown in Table 1.

(B) The bactericidal effects of a combination of ethyl alcohol and an organic acid was examined in the same ways as in (A) above. The organic acids tested were lactic acid, acetic acid, citric acid, tartaric acid, gluconic acid, malic acid, ascorbic acid and phytic acid. The results obtained with a contact time of 30 seconds are shown in Table 2.

TABLE 1

| Type and concentration (%) of the inorganic acid | | Concentration of ethyl alcohol (%) 40 | 35 | 30 | 25 | 20 | 15 | 10 | 5 | 0 |
|---|---|---|---|---|---|---|---|---|---|---|
| Phosphoric acid | 20 | − | − | − | − | − | − | − | − | + |
| | 10 | − | − | − | − | − | − | + | + | + |
| | 5 | − | − | − | − | − | − | + | + | + |
| | 3 | − | − | − | − | − | + | + | + | + |
| | 1 | − | − | − | − | − | + | + | + | + |
| | 0.5 | − | − | + | + | + | + | + | + | + |
| | 0 | − | + | + | + | + | + | + | + | + |
| Sodium ultra phosphate | 0.5 | − | − | − | − | − | + | + | + | + |
| | 0.3 | − | − | − | − | + | + | + | + | + |
| | 0.1 | − | − | − | + | + | + | + | + | + |
| | 0.05 | − | − | + | + | + | + | + | + | + |
| | 0 | − | + | + | + | + | + | + | + | + |
| Acidic sodium pyro-phosphate | 0.5 | − | − | − | + | + | + | + | + | + |
| | 0.3 | − | − | − | + | + | + | + | + | + |
| | 0.1 | − | − | + | + | + | + | + | + | + |
| | 0.05 | − | + | + | + | + | + | + | + | + |
| | 0 | − | + | + | + | + | + | + | + | + |
| Sodium hexameta-phosphate | 0.5 | − | − | − | + | + | + | + | + | + |
| | 0.3 | − | − | + | + | + | + | + | + | + |
| | 0.1 | − | + | + | + | + | + | + | + | + |
| | 0.005 | − | + | + | + | + | + | + | + | + |
| | 0 | − | + | + | + | + | + | + | + | + |
| Nitric acid | 0.1 | − | − | − | − | − | − | − | − | − |
| | 0.05 | − | − | − | − | + | + | + | + | + |
| | 0.03 | − | − | − | − | + | + | + | + | + |
| | 0.01 | − | − | − | − | + | + | + | + | + |
| | 0.005 | − | − | − | + | + | + | + | + | + |
| | 0 | − | + | + | + | + | + | + | + | + |

TABLE 2

| Type and concentration (%) of the organic acid | | Concentration of ethyl alcohol (%) 40 | 35 | 30 | 25 | 20 | 15 | 10 | 5 | 0 |
|---|---|---|---|---|---|---|---|---|---|---|
| Lactic acid | 20 | − | − | − | − | − | − | − | − | + |
| | 10 | − | − | − | − | − | − | − | − | + |
| | 5 | − | − | − | − | − | − | − | + | + |
| | 3 | − | − | − | − | − | − | − | + | + |
| | 1 | − | − | − | − | − | − | + | + | + |
| | 0.5 | − | − | − | − | − | − | + | + | + |
| | 0 | − | + | + | + | + | + | + | + | + |
| Acetic acid | 20 | − | − | − | − | − | − | − | − | + |
| | 10 | − | − | − | − | − | − | − | − | + |
| | 5 | − | − | − | − | − | + | + | + | + |
| | 3 | − | − | − | − | + | + | + | + | + |
| | 1 | − | − | − | − | + | + | + | + | + |
| | 0.5 | − | − | − | + | + | + | + | + | + |
| | 0 | − | + | + | + | + | + | + | + | + |
| Citric acid | 20 | − | − | − | + | + | + | + | + | + |
| | 10 | − | − | − | + | + | + | + | + | + |
| | 5 | − | − | + | + | + | + | + | + | + |
| | 3 | − | − | + | + | + | + | + | + | + |
| | 1 | − | + | + | + | + | + | + | + | + |
| | 0.5 | − | + | + | + | + | + | + | + | + |
| | 0 | − | + | + | + | + | + | + | + | + |

TABLE 2-continued

| Type and concentration (%) of the organic acid | | Concentration of ethyl alcohol (%) 40 | 35 | 30 | 25 | 20 | 15 | 10 | 5 | 0 |
|---|---|---|---|---|---|---|---|---|---|---|
| Tartaric acid | 20 | − | − | − | + | + | + | + | + | + |
| | 10 | − | − | − | + | + | + | + | + | + |
| | 5 | − | − | + | + | + | + | + | + | + |
| | 3 | − | − | + | + | + | + | + | + | + |
| | 1 | − | − | + | + | + | + | + | + | + |
| | 0.5 | − | + | + | + | + | + | + | + | + |
| | 0 | − | + | + | + | + | + | + | + | + |
| Gluconic acid | 20 | − | − | − | + | + | + | + | + | + |
| | 10 | − | − | − | + | + | + | + | + | + |
| | 5 | − | − | + | + | + | + | + | + | + |
| | 3 | − | − | + | + | + | + | + | + | + |
| | 1 | − | − | + | + | + | + | + | + | + |
| | 0.5 | − | + | + | + | + | + | + | + | + |
| | 0 | − | + | + | + | + | + | + | + | + |
| Malic acid | 10 | − | − | − | − | − | + | + | + | + |
| | 5 | − | − | − | − | + | + | + | + | + |
| | 3 | − | − | − | − | + | + | + | + | + |
| | 1 | − | − | − | + | + | + | + | + | + |
| | 0 | − | + | + | + | + | + | + | + | + |
| Ascorbic acid | 7.5 | − | − | − | − | − | + | + | + | + |
| | 3.75 | − | − | − | − | + | + | + | + | + |
| | 2.25 | − | − | − | + | + | + | + | + | + |
| | 0.75 | − | − | − | + | + | + | + | + | + |
| | 0 | − | + | + | + | + | + | + | + | + |
| Phytic acid | 20 | − | − | − | − | − | − | − | − | + |
| | 10 | − | − | − | − | − | − | + | + | + |
| | 5 | − | − | − | − | − | − | + | + | + |
| | 2.5 | − | − | − | − | − | + | + | + | + |
| | 1.25 | − | − | − | − | − | + | + | + | + |
| | 0.61 | − | − | − | − | + | + | + | + | + |
| | 0.31 | − | − | − | − | + | + | + | + | + |
| | 0.15 | − | − | − | − | + | + | + | + | + |
| | 0 | − | + | + | + | + | + | + | + | + |

The results given in Table 1 demonstrate that a marked synergistic effect was noted in a combination of ethyl alcohol with phosphoric acid. It is also seen from Table 2 that a combination of ethyl alcohol with lactic acid or acetic acid produces an excellent synergistic effect.

(C) Because a strong effect was noted in the combination of ethyl alcohol with phosphoric acid or lactic acid, a combination of ethyl alcohol, phosphoric acid and lactic acid was examined for bactericidal activity in the same way as in (A) above. The results obtained after a contact time of 30 seconds are shown in Table 3.

It is seen from Table 3 that the effect of the combination of these three chemicals was much stronger than that expected from the combination of ethyl alcohol and lactic acid or phosphoric acid.

The experimental results thus obtained show that when ethyl alcohol or the acids were individually used for sterilization, the various adverse effects mentioned hereinabove could not be avoided, whereas the combined use of ethyl alcohol and an organic acid and/or an inorganic acid, particularly the combined use of ethyl alcohol, lactic acid and phosphoric acid, greatly reduced the required concentrations of the individual chemicals and made possible effective sterilization without giving rise to problems of a sour taste, odor, degeneration, etc.

TABLE 3

| Phosphoric acid (%) | Lactic acid (%) | Concentration of ethyl alcohol (%) 40 | 35 | 30 | 25 | 20 | 15 | 10 | 5 | 3 | 1 | 0.5 | 0 |
|---|---|---|---|---|---|---|---|---|---|---|---|---|---|
| 0 | 20 | − | − | − | − | − | − | − | − | + | + | + | + |
| | 10 | − | − | − | − | − | − | − | − | + | + | + | + |

TABLE 3-continued

| Phosphoric acid (%) | Lactic acid (%) | Concentration of ethyl alcohol (%) 40 | 35 | 30 | 25 | 20 | 15 | 10 | 5 | 3 | 1 | 0.5 | 0 |
|---|---|---|---|---|---|---|---|---|---|---|---|---|---|
| | 5 | − | − | − | − | − | − | − | + | + | + | + | + |
| | 3 | − | − | − | − | − | − | − | + | + | + | + | + |
| | 1 | − | − | − | − | − | − | + | + | + | + | + | + |
| | 0.5 | − | − | − | − | − | − | + | + | + | + | + | + |
| | 0 | − | + | + | + | + | + | + | + | + | + | + | + |
| 0.1 | 20 | − | − | − | − | − | − | − | − | − | − | + | + |
| | 10 | − | − | − | − | − | − | − | − | − | − | + | + |
| | 5 | − | − | − | − | − | − | − | − | − | + | + | + |
| | 3 | − | − | − | − | − | − | − | − | − | + | + | + |
| | 1 | − | − | − | − | − | − | + | + | + | + | + | + |
| | 0.5 | − | − | − | − | − | − | + | + | + | + | + | + |
| | 0 | − | − | + | + | + | + | + | + | + | + | + | + |
| 0.5 | 20 | − | − | − | − | − | − | − | − | − | − | − | + |
| | 10 | − | − | − | − | − | − | − | − | − | − | − | + |
| | 5 | − | − | − | − | − | − | − | − | − | − | − | + |
| | 3 | − | − | − | − | − | − | − | − | − | + | + | + |
| | 1 | − | − | − | − | − | − | − | + | + | + | + | + |
| | 0.5 | − | − | − | − | − | − | + | + | + | + | + | + |
| | 0 | − | − | + | + | + | + | + | + | + | + | + | + |
| 1.0 | 20 | − | − | − | − | − | − | − | − | − | − | − | + |
| | 10 | − | − | − | − | − | − | − | − | − | − | − | + |
| | 5 | − | − | − | − | − | − | − | − | − | − | − | + |
| | 3 | − | − | − | − | − | − | − | − | − | − | − | + |
| | 1 | − | − | − | − | − | − | − | − | − | + | + | + |
| | 0.5 | − | − | − | − | − | − | − | − | + | + | + | + |
| | 0 | − | − | − | − | − | + | + | + | + | + | + | + |

EXPERIMENTAL EXAMPLE 2

Since lactic acid and phosphoric acid are acidic substances, the pH of the bactericidal solution which is decreased as a result of using these acids presumably contributes also to the bactericidal activity of the solution. To confirm this, the following experiment was performed.

A mixture of ethyl alcohol, phosphoric acid and lactic acid was prepared. The concentrations of ethyl alcohol and phosphoric acid were fixed at 10% and 0.1%, respectively, whereas the concentration of lactic acid was varied within the range of 3 to 20% as shown in Table 4. The pH of the mixture was adjusted to 5-1 with 1N—NaOH or HCl at the time of application. The bactericidal effect of the mixture was examined in the same way as in Experimental Example 1, (A). The time of contact between the sample bacterial suspension and the sample bactericidal mixture was varied between 30 seconds and 10 minutes. The results are shown in Table 4. These results show that a pH of 4.0 or below is desirable.

Accordingly, organic acids and inorganic acids other than lactic acid and phosphoric acid can fully exhibit a bactericidal effect by using them together with ethyl alcohol. For example, a combination of ethyl alcohol, lactic acid and another organic acid or salt, a combination of ethyl alcohol and, phosphoric acid and another inorganic acid or salt, or a combination of ethyl alcohol, another organic acid and another inorganic acid is effective when a solution of such a combination is adjusted to not more than 4.0.

TABLE 4

| pH of the solution during contact | Lactic acid (%) | Contacting time 30 seconds | 1 minute | 5 minutes | 10 minutes |
|---|---|---|---|---|---|
| 1 and 2 | 3 | − | − | − | − |
| | 5 | − | − | − | − |
| | 10 | − | − | − | − |
| | 15 | − | − | − | − |
| | 20 | − | − | − | − |
| 3 | 3 | − | − | − | − |
| | 5 | − | − | − | − |
| | 10 | − | − | − | − |
| | 15 | − | − | − | − |
| | 20 | − | − | − | − |
| 4 | 3 | + | + | + | − |
| | 5 | + | + | − | − |
| | 10 | + | − | − | − |
| | 15 | − | − | − | − |
| | 20 | − | − | − | − |
| 5 | 3 | + | + | + | + |
| | 5 | + | + | + | + |
| | 10 | + | + | + | + |
| | 15 | + | + | + | − |
| | 20 | + | + | + | − |

(Note):
Ethyl alcohol 10%; phosphoric acid 0.1%.

EXPERIMENTAL EXAMPLE 3

Three mixtures having the following compositions were prepared on the basis of the results of Experimental Examples 1 and 2, and examined for bactericidal effect in the same way as in Example 1, (a). The results are shown in Table 5.

| | |
|---|---|
| Mixture A | |
| Ethyl alcohol | 87.0% |
| Lactic acid | 8.7% |
| Phosphoric acid | 4.3% |
| Total | 100% |
| Mixture B | |
| Ethyl alcohol | 61.7% |
| Lactic acid | 37.0% |
| Phosphoric acid | 1.3% |
| Total | 100% |
| Mixture C | |
| Ethyl alcohol | 37.0% |
| Lactic acid | 61.7% |
| Phosphoric acid | 1.3% |
| Total | 100% |

TABLE 5

| Chemicals | Concentration (%) | Concentrations of the ingredients in the aqueous solution (%) Ethyl alcohol | Lactic acid | Phosphoric acid | Contacting time 30 seconds | 1 minute | 5 minutes | 10 minutes |
|---|---|---|---|---|---|---|---|---|
| Mixture A | 10 | 8.70 | 0.87 | 0.43 | − | − | − | − |
| | 7 | 6.09 | 0.609 | 0.301 | − | − | − | − |
| | 5 | 4.35 | 0.435 | 0.215 | + | + | + | − |
| | 3 | 2.61 | 0.261 | 0.129 | + | + | + | − |
| | 1 | 0.87 | 0.087 | 0.043 | + | + | + | + |
| Mixture B | 10 | 6.17 | 3.70 | 0.13 | − | − | − | − |
| | 7 | 4.32 | 2.59 | 0.091 | − | − | − | − |
| | 5 | 3.09 | 1.85 | 0.065 | − | − | − | − |
| | 3 | 1.85 | 1.11 | 0.039 | + | + | + | − |

TABLE 5-continued

| Chemicals | Concentration (%) | Concentrations of the ingredients in the aqueous solution (%) Ethyl alcohol | Lactic acid | Phosphoric acid | Contacting time 30 seconds | 1 minute | 5 minutes | 10 minutes |
|---|---|---|---|---|---|---|---|---|
| | 1 | 0.617 | 0.370 | 0.013 | + | + | + | + |
| Mixture C | 10 | 3.70 | 6.17 | 0.13 | − | − | − | − |
| | 7 | 2.59 | 4.319 | 0.091 | − | − | − | − |
| | 5 | 1.85 | 3.085 | 0.065 | − | − | − | − |
| | 3 | 1.11 | 1.851 | 0.039 | + | + | + | − |
| | 1 | 0.370 | 0.617 | 0.013 | + | + | + | + |
| Lactic acid | 20 | | | | + | + | + | + |
| Phosphoric acid | 20 | | | | + | + | + | + |
| Ethyl alcohol | 40 | | | | − | − | − | − |
| | 35 | | | | + | + | + | + |
| | 30 | | | | + | + | + | + |
| | 20 | | | | + | + | + | + |
| Not added | 0 | | | | + | + | + | + |

As shown in Table 5, the bactericidal effect was strongest with the mixture C and least strong with the mixture A, and the mixture B comes in between. Each of the mixtures showed a bactericidal effect when the concentrations of ethyl alcohol, lactic acid and phosphoric acid were much smaller than the effective concentrations of these components used individually. Thus, a marked synergistic effect was noted.

EXAMPLE 1

The bactericidal effects of each of the chemicals shown in Table 6 on bacteria adhering to "crab leg-like fish-cake (kamaboko-like product)" whose infection by coliform bacteria is especially notable were examined.

| | |
|---|---|
| Refrigerated Alaska pollack | 1 kg |
| Salt | 30 g |
| L-glutamic acid | 100 g |
| Crab flavor | 5 g |
| Potato starch | 50 g |
| Ice water | 300 g |
| Total | 1485 g |

A minced flesh of the above composition was molded into a block having a weight of about 1 kg and attached to a plate. The product was held at 40° C. for 1 hour, and its surface was colored with natural red dye. The product was steamed at 90° C. for 1 hour and cooled.

The plate was removed from the resulting product, and dipped for 10 seconds in a suspension of *Escherichia coli* (NIHJ-JC-2) to cause the bacteria to adhere fully. The contaminated block was then dipped for 30 seconds in a water solution of each of the mixtures A, B and C in the concentrations shown in Table 6. Immediately then, it was withdrawn. The standard plate count was measured by a conventional plate dilution method using a standard agar culture medium. The number of coliform organisms was measured by the plate dilution method using a desoxycholate agar culture medium. For comparison, the number of bacteria was measured in the same way immediately after dipping of the block in the bacterial suspension, or after further dipping it in hydrogen peroxide or ethyl alcohol solution. The results are summarized in Table 6.

The results show that the bactericidal agent of the invention can perform complete sterilization at an extremely low concentration which was 1/10 to 1/14 of the effective concentration of ethyl alcohol alone. The concentration of the required concentration of ethyl alcohol in the mixtures was much lower, and is about 1/11 to 1/38 of that required when ethyl alcohol is used alone. The same can be said with regard to the other components. This means that the combination of chemicals in accordance with this invention produces a marked synergistic effect, and therefore, can simultaneously solve the conventional problems of the quality of foods, the working environment, safety, etc.

TABLE 6

(fish-cake product)

| Chemicals | Concentrations of the chemicals (%) | Concentrations (%) Ethyl alcohol | Lactic acid | Phosphoric acid | After dipping treatment Standard plate count (cells/g) | Number of coliform organisms (cells/g) |
|---|---|---|---|---|---|---|
| Non-treated (immediately after attachment of bacteria) | | | | | $9.9 \times 10^4$ | $1.3 \times 10^3$ |
| Distilled water | | | | | $3.0 \times 10^3$ | $2.1 \times 10^2$ |
| Hydrogen peroxide | 0.05 | | | | $2.1 \times 10^3$ | $1.1 \times 10^2$ |
| Mixture A | 10 | 8.70 | 0.87 | 0.43 | 0 | 0 |
| | 7 | 6.09 | 0.609 | 0.301 | 0 | 0 |
| | 5 | 4.35 | 0.435 | 0.215 | $9.2 \times 10^2$ | $6.3 \times 10$ |
| | 3 | 2.61 | 0.261 | 0.129 | $2.5 \times 10^3$ | $1.80 \times 10^2$ |
| | 1 | 0.87 | 0.087 | 0.043 | $2.7 \times 10^3$ | $1.90 \times 10^2$ |
| Mixture B | 10 | 6.17 | 3.70 | 0.13 | 0 | 0 |
| | 7 | 4.32 | 2.59 | 0.091 | 0 | 0 |
| | 5 | 3.085 | 1.85 | 0.065 | 0 | 0 |
| | 3 | 1.851 | 1.11 | 0.039 | $8.1 \times 10^2$ | $5.2 \times 10$ |
| Mixture C | 10 | 370 | 6.17 | 0.13 | 0 | 0 |

TABLE 6-continued (fish-cake product)

| Chemicals | Concentrations of the chemicals (%) | Concentrations (%) Ethyl alcohol | Lactic acid | Phosphoric acid | After dipping treatment Standard plate count (cells/g) | Number of coliform organisms (cells/g) |
|---|---|---|---|---|---|---|
| | 7 | 2.59 | 4.319 | 0.091 | 0 | 0 |
| | 5 | 1.85 | 3.085 | 0.065 | 0 | 0 |
| | 3 | 1.11 | 1.851 | 0.039 | 2.5 × $10^2$ | 6.1 × 10 |
| | 1 | 0.370 | 0.617 | 0.013 | 2.7 × $10^2$ | 1.75 × $10^2$ |
| Ethyl alcohol | 70 | | | | 0 | 0 |
| | 60 | | | | 2.5 × $10^3$ | 1.5 × $10^2$ |

In order to examine the effects of the bactericidal agent of the invention on the flavor of foods, a paste product produced as above was removed from the plate, and immediately then, dipped for 30 seconds in an aqueous solution of each of various chemicals. It was then subjected to an organoleptic test by a panel of ten persons for an unusual taste or an unusual odor. The results are shown in Table 7.

It is seen from Table 7 that the bactericides of the invention show no effect on the flavor of foods when their concentrations were not more than 30%. Since the concentration of 30% is much higher than the effective concentrations shown in Table 6, it is clear that the bactericides of the invention can be used without any deleterious effect on the flavor of foods.

TABLE 7

(fish-cake product)

| Chemicals | Concentrations of the chemicals (%) | Number of the panelists who felt an unusual taste or an unusual odor out of 10 |
|---|---|---|
| Distilled water | — | 0 |
| Hydrogen peroxide | 0.05 | 0 |
| Mixture A | 40 | 4 |

TABLE 7-continued (fish-cake product)

| Chemicals | Concentrations of the chemicals (%) | Number of the panelists who felt an unusual taste or an unusual odor out of 10 |
|---|---|---|
| | 30 | 0 |
| Mixture B | 40 | 5 |
| | 30 | 0 |
| Mixture C | 40 | 8 |
| | 30 | 0 |
| Ethyl alcohol | 70 | 10 |
| | 60 | 8 |

EXAMPLE 2

In this Example, the bactericidal effects of each of the chemicals shown in Table 8 and 9 on onion (about 100 g) and cucumber (about 100 g) whose infection by noxious bacteria was heaviest among edible vegetables were examined in the same way as in Example 1. The results are shown in Tables 8 and 9.

The cucumber was subjected to an organoleptic test in the same way as in Example 1. The results are shown in Table 10.

TABLE 8

(onion)

| Chemicals | Concentrations of the chemicals (%) | Concentrations (%) Ethyl alcohol | Lactic acid | Phosphoric acid | After dipping treatment Standard plate count (cells/g) | Number of coliform organisms (cells/g) |
|---|---|---|---|---|---|---|
| Non-treated (immediately after attachment of bacteria) | — | | | | 5.3 × $10^6$ | 1.7 × $10^4$ |
| Blanching* | — | | | | 2.5 × $10^2$ | 0 |
| Distilled water | — | | | | 2.25 × $10^6$ | 8.4 × $10^4$ |
| Hydrogen peroxide | 0.02 | | | | 3.3 × $10^6$ | 3.0 × $10^2$ |
| Mixture A | 10 | 8.70 | 0.87 | 0.43 | 0 | 0 |
| | 7 | 6.09 | 0.609 | 0.301 | 4.4 × $10^4$ | 0 |
| | 5 | 4.35 | 0.435 | 0.215 | 2.5 × $10^6$ | 6.7 × $10^3$ |
| | 3 | 2.61 | 0.261 | 0.129 | 2.11 × $10^6$ | 5.4 × $10^4$ |
| | 1 | 0.87 | 0.087 | 0.043 | 2.80 × $10^6$ | 6.9 × $10^4$ |
| Mixture B | 10 | 6.17 | 3.70 | 0.13 | 0 | 0 |
| | 7 | 4.319 | 2.59 | 0.091 | 0 | 0 |
| | 5 | 3.085 | 1.85 | 0.065 | 0 | 0 |
| | 3 | 1.851 | 1.11 | 0.039 | 2.30 × $10^3$ | 5.2 × $10^3$ |
| | 1 | 0.677 | 0.370 | 0.013 | 2.18 × $10^6$ | 6.7 × $10^4$ |
| Mixture C | 10 | 3.70 | 6.17 | 0.13 | 0 | 0 |
| | 7 | 2.59 | 4.319 | 0.091 | 0 | 0 |
| | 5 | 1.85 | 3.085 | 0.065 | 0 | 0 |
| | 3 | 1.11 | 1.851 | 0.039 | 5.1 × $10^3$ | 5.9 × $10^2$ |
| | 1 | 0.370 | 0.617 | 0.013 | 2.12 × $10^6$ | 8.2 × $10^4$ |
| Ethyl alcohol | 70 | | | | 3.8 × $10^3$ | 1.3 × $10^2$ |

*Dipped in warm water at 80° C. for 30 seconds.

TABLE 9

(cucumber)

| Chemicals | Concentrations of the chemicals (%) | Concentrations (%) Ethyl alcohol | Lactic acid | Phosphoric acid | After dipping treatment Standard plate count (cells/g) | Number of coliform organisms (cells/g) |
|---|---|---|---|---|---|---|
| Non-treated (immediately after attachment of bacteria) | | | | | $7.9 \times 10^5$ | $2.4 \times 10^4$ |
| Blanching* | | | | | 0 | 0 |
| Distilled water | — | | | | $1.45 \times 10^3$ | $4.1 \times 10^3$ |
| Hydrogen peroxide | 0.02 | | | | $3.9 \times 10^4$ | $9.2 \times 10^3$ |
| Mixture A | 10 | 8.70 | 0.87 | 0.43 | 0 | 0 |
| | 7 | 6.09 | 0.609 | 0.301 | 0 | 0 |
| | 5 | 4.35 | 0.435 | 0.215 | $5.3 \times 10^3$ | $4.6 \times 10^2$ |
| | 3 | 2.61 | 0.261 | 0.129 | $8.9 \times 10^4$ | $3.9 \times 10^3$ |
| | 1 | 0.87 | 0.087 | 0.043 | $1.29 \times 10^5$ | $4.0 \times 10^3$ |
| Mixture B | 10 | 6.17 | 3.70 | 0.13 | 0 | 0 |
| | 7 | 4.319 | 2.59 | 0091 | 0 | 0 |
| | 5 | 3.085 | 1.85 | 0.065 | 0 | 0 |
| | 3 | 1.831 | 1.11 | 0.039 | $6.9 \times 10^3$ | $2.9 \times 10^2$ |
| | 1 | 0.617 | 0.370 | 0.013 | $7.2 \times 10^4$ | $3.8 \times 10^3$ |
| Mixture C | 10 | 3.70 | 6.17 | 0.13 | 0 | 0 |
| | 7 | 2.59 | 4.319 | 0.091 | 0 | 0 |
| | 5 | 1.85 | 3.085 | 0.065 | 0 | 0 |
| | 3 | 1.11 | 1.851 | 0.039 | $7.3 \times 10^4$ | $3.7 \times 10^2$ |
| | 1 | 0.370 | 0.617 | 0.013 | $1.32 \times 10^5$ | $3.7 \times 10^3$ |
| Ethyl alcohol | 70 | | | | $8.8 \times 10^3$ | $9.0 \times 10^2$ |

*Dipped in warm water at 80° C. for 30 seconds.

TABLE 10

(cucumber)

| Chemicals | Concentration (%) | Number of panelists who felt an unusual taste or an unusual odor out of 10 |
|---|---|---|
| Blanching | | 5 |
| Distilled water | — | 0 |
| Hydrogen peroxide | 0.05 | 0 |
| Mixture A | 40 | 4 |
| | 30 | 0 |
| Mixture B | 40 | 6 |
| | 30 | 0 |
| Mixture C | 40 | 9 |
| | 30 | 1 |
| | 20 | 0 |
| Ethyl alcohol | 70 | 10 |
| | 60 | 9 |

EXAMPLE 3

In this Example, the mixture B shown in Experimental Example 3 was used to kill bacteria adhering to vegetables.

Cucumber and cabbage cut into four were washed with water, and dipped in each of the chemicals shown in Table 11, and the number of bacteria was examined by the conventional plate diluting method in the same way as in Example 1. The results are shown in Table 11.

TABLE 11

| Vegetable | Chemical | Concentration of the chemical (%) | Dipping time (minutes) | After dipping treatment Standard plate count (cells/g) | Number of coliform organisms (cells/g) |
|---|---|---|---|---|---|
| Cucumber* | Only washed with water | | | $4.0 \times 10^6$ | $1.56 \times 10^3$ |
| | Mixture B | 2% | 10 | $3.9 \times 10^5$ | 0 |
| | | | 20 | $7.2 \times 10^4$ | 0 |
| | | | 30 | $5.4 \times 10^4$ | 0 |
| | | 1% | 30 | $2.4 \times 10^4$ | 0 |
| | Sodium hypochlorite (as available Cl) | 200 ppm | 30 | $2.4 \times 10^5$ | $8.5 \times 10^2$ |
| Cabbage* | Only washed with water | | | $3.1 \times 10^5$ | $1.3 \times 10^5$ |
| | Mixture B | 1.0% | 30 | $7.9 \times 10^5$ | 0 |
| | | 0.7% | 30 | $3.2 \times 10^2$ | 0 |
| | | 0.5% | 30 | $2.8 \times 10^2$ | $5.0 \times 10$ |

*The cucumber was sliced at the surface portion, and the cabbage was the one sampled at random from many cabbages. The number of bacteria per gram was examined using 10 g each of these samples.

EXAMPLE 4

The bactericidal effects of each of the chemicals shown in Table 12 on bacteria adhering to the surface of chicken (broiler) were examined.

The test was carried out in the same way as in Example 1 using about 51 g of the flesh taken from near the wing of a chicken. The results are shown in Table 12, and demonstrate the marked effects of the bactericides of the invention.

When the above test was repeated except that the whole flesh of a chicken was used instead of the flesh near the wing, bacteria (general bacteria and coliform organisms) were not detected when the mixture A was used in an amount of 5%, the mixture B, in an amount of 3%, and the mixture C, in an amount of 3%. At lower concentrations than those shown in Table 12, complete sterilization was obtained.

By the same tests as above, it was confirmed that the bactericides of the invention are equally effective for beef, pork and fresh seafoods.

EXAMPLE 5

The bactericidal effects of the chemicals shown in Table 13 were tested on chicken eggs.

*Escherichia coli* was caused to adhere to about 67 g of eggs in the same way as in Example 1, and the eggs were then dipped for 30 seconds in an aqueous solution of each of the chemicals. Then, the surfaces of the eggs were wiped off, and the standard plate count and the number of coliform organisms were measured. The results are shown in Table 13.

TABLE 12

(chicken)

| Chemical | Concentration of the chemical (%) | Concentration of the ingredients (%) Ethyl alcohol | Lactic acid | Phosphoric acid | After dipping treatment Standard plate count (cells/10 × 10 cm²) | Number of coliform organisms (cells/10 × 10 cm²) |
|---|---|---|---|---|---|---|
| Non-treated (immediately after bacteria attachment) | — | | | | $6.3 \times 10^6$ | $3.8 \times 10^4$ |
| Distilled water | — | | | | $4.2 \times 10^6$ | $3.5 \times 10^4$ |
| Sodium hypochlorite | 0.02 | | | | $3.7 \times 10^6$ | $3.9 \times 10^4$ |
| Mixture A | 10 | 8.70 | 0.87 | 0.43 | 0 | 0 |
| | 7 | 6.09 | 0.609 | 0.301 | 0 | 0 |
| | 5 | 4.35 | 0.435 | 0.215 | $3.9 \times 10^5$ | $8.7 \times 10^2$ |
| | 3 | 2.61 | 0.261 | 0.129 | $3.8 \times 10^6$ | $2.9 \times 10^4$ |
| | 1 | 0.87 | 0.087 | 0.043 | $4.1 \times 10^6$ | $3.7 \times 10^4$ |
| Mixture B | 10 | 6.17 | 3.70 | 0.13 | 0 | 0 |
| | 7 | 4.319 | 2.59 | 0.091 | 0 | 0 |
| | 5 | 3.085 | 1.85 | 0.065 | 0 | 0 |
| | 3 | 1.851 | 1.11 | 0.039 | $5.1 \times 10^4$ | $7.8 \times 10^2$ |
| | 1 | 0.617 | 0.370 | 0.016 | $3.9 \times 10^6$ | $2.9 \times 10^4$ |
| Mixture C | 10 | 3.70 | 6.17 | 0.13 | 0 | 0 |
| | 7 | 2.59 | 4.319 | 0.091 | 0 | 0 |
| | 5 | 1.85 | 3.085 | 0.065 | 0 | 0 |
| | 3 | 1.11 | 1.851 | 0.039 | $4.8 \times 10^4$ | $6.7 \times 10^2$ |
| | 1 | 0.370 | 0.617 | 0.013 | $3.7 \times 10^6$ | $3.2 \times 10^4$ |
| Ethyl alcohol | 70 | | | | $9.8 \times 10^5$ | $2.9 \times 10^4$ |

It is seen from Table 13 that the bactericides of the invention show a marked effect as a bactericidal treating agent for eggs.

TABLE 13

(chicken eggs)

| Chemical | Concentration of the chemical (%) | Concentration of the ingredients (%) Ethyl alcohol | Lactic acid | Phosphoric acid | After dipping treatment Standard plate count (cells/10 × 10 cm²) | Number of coliform organisms (cells/10 × 10 cm²) |
|---|---|---|---|---|---|---|
| Non-treated (immediately after bacteria attachment) | — | | | | $5.5 \times 10^4$ | $7.5 \times 10^2$ |
| Distilled water | — | | | | $2.8 \times 10^4$ | $5.8 \times 10^2$ |
| Sodium hypochlorite | 0.02 | | | | $8.1 \times 10^3$ | $4.1 \times 10^2$ |
| Mixture A | 10 | 8.70 | 0.87 | 0.43 | 0 | 0 |
| | 7 | 6.09 | 0.609 | 0.301 | 0 | 0 |
| | 5 | 4.35 | 0.435 | 0.215 | $2.7 \times 10^3$ | $9.8 \times 10$ |
| | 3 | 2.61 | 0.261 | 0.129 | $2.5 \times 10^4$ | $5.3 \times 10^2$ |
| | 1 | 0.87 | 0.087 | 0.043 | $2.5 \times 10^4$ | $5.2 \times 10^2$ |
| Mixture B | 10 | 6.17 | 3.70 | 0.13 | 0 | 0 |
| | 7 | 4.319 | 2.59 | 0.091 | 0 | 0 |
| | 5 | 3.085 | 1.85 | 0.065 | 0 | 0 |
| | 3 | 1.851 | 1.11 | 0.039 | $5.1 \times 10^2$ | $9.7 \times 10$ |
| | 1 | 0.617 | 0.370 | 0.013 | $3.1 \times 10^4$ | $4.9 \times 10^2$ |
| Mixture C | 10 | 3.70 | 6.17 | 0.13 | 0 | 0 |
| | 7 | 2.59 | 4.319 | 0.091 | 0 | 0 |
| | 5 | 1.85 | 3.085 | 0.065 | 0 | 0 |
| | 3 | 1.11 | 1.851 | 0.039 | $4.8 \times 10^3$ | $5.8 \times 10$ |
| | 1 | 0.370 | 0.617 | 0.013 | $8.0 \times 10^4$ | $4.2 \times 10^2$ |
| Ethyl alcohol | 70 | | | | $3.9 \times 10^3$ | $5.1 \times 10$ |

EXAMPLE 6

In this Example, the bactericidal effects of each of the chemicals shown in Table 14 on bacteria adhering to the surface of ham were tested.

Salt (1.5%), 120 ppm of sodium nitrite, 550 ppm of sodium erythorbate and 0.3% of sodium tripolyphosphate were uniformly injected into about 2 kg of meat taken from the ham portion of a hog. The meat was then rubbed and kneaded, wrapped with a cotton cloth and tied with a thread. It was then dried at 40° C. for 3 hours and smoked at 57° C. for 4 hours to produce a ham. The ham was stored at 0° C. overnight, and used as a test sample.

A pre-cultivated suspension of *Escherichia coli* and *Lactobacillus vulgaricus* was suspended in physiological saline to prepare a bacterial suspension.

The ham sample was cut into blocks each weighing about 200 g. The blocks were dipped for 5 seconds in the bacterial suspension to cause the bacteria to adhere to the surface of the blocks. The blocks were then dipped in each of the bactericidal solutions shown in Table 14 for a predetermined period of time, and withdrawn. Then, the surface portion of each block was cut off aseptically, and homogenized. The number of bacteria was measured. The results are shown in Table 14.

TABLE 14

| Treatment | | Bacteria | Dipping time versus bacteria count | | |
|---|---|---|---|---|---|
| | | | 30 seconds | 1 minute | 5 minutes |
| Dipping in water only | | coliform organisms | $5.1 \times 10^3$ | $2.6 \times 10^3$ | $1.55 \times 10^4$ |
| | | lactic acid bacteria | $4.3 \times 10^4$ | $2.6 \times 10^4$ | $5.4 \times 10^4$ |
| | | standard plate count | $3.7 \times 10^4$ | $2.2 \times 10^4$ | $5.3 \times 10^4$ |
| Mixture B | 5% | coliform organisms | $1.4 \times 10^2$ | $1.6 \times 10^2$ | — |
| | | lactic acid bacteria | $4.3 \times 10^3$ | $6.7 \times 10^3$ | $3.0 \times 10^3$ |
| | | standard plate count | $2.9 \times 10^3$ | $4.7 \times 10^3$ | $3.5 \times 10^3$ |
| | 10% | coliform organisms | — | — | — |
| | | lactic acid bacteria | $6.9 \times 10^2$ | $4.3 \times 10^2$ | $1.1 \times 10^2$ |
| | | standard plate count | $2.1 \times 10^3$ | $1.75 \times 10^3$ | $3.8 \times 10^2$ |
| Sodium | 500 ppm | coliform organisms | | $3.8 \times 10^3$ | $7.5 \times 10^2$ |
| hypochlorite | | lactic acid bacteria | | $6.6 \times 10^4$ | $5.8 \times 10^3$ |
| (as available Cl) | | standard plate count | | $4.2 \times 10^4$ | $6.4 \times 10^3$ |
| Ethyl alcohol | 60% | coliform organisms | $3.9 \times 10^2$ | $1.6 \times 10^2$ | $1.2 \times 10$ |
| | | lactic acid bacteria | $1.8 \times 10^3$ | $3.4 \times 10^3$ | $1.5 \times 10^2$ |
| | | standard plate count | $1.8 \times 10^3$ | $5.4 \times 10^3$ | $5.1 \times 10^2$ |
| | 70% | coliform organisms | $2.0 \times 10^2$ | $1.4 \times 10^2$ | — |
| | | lactic acid bacteria | $7.8 \times 10^2$ | $6.1 \times 10^2$ | $1.1 \times 10^2$ |
| | | standard plate count | $2.2 \times 10^3$ | $1.9 \times 10^3$ | $5.5 \times 10^2$ |

The bacterial count is the number of bacteria per g, (—) represents "negative".

EXAMPLE 7

In the process of producing Vienna sausage, before packaging, the heat-treated sausage is usually (1) cooled and carried to a clean room, (2) cut by a drum cutter, (3) carried on a conveyor, (4) sent to an aligner, and (5) put into a bucket.

In this Example, the following two tests were conducted in order to examine the bactericidal effect of the bactericide (mixture B) of the invention.

In the first test showing a conventional process, the standard plate count, the number of lactic acid bacteria, and the presence or absence (positive or negative) of coliform organisms were determined with regard to the sausage (1) in the clean room, and the sauges (6) which was passed through the drum cutter (2), conveyor (3), the aligner (4), and bucket (5).

In the second test showing the process of the invention, the same test as above was carried out with regard to the sausage (1') treated with the bactericide and placed within a clean room, the drum cutter (2') treated with the bactericide, the conveyor (3') treated with the bactericide, the aligner (4') treated with the bactericide, and the bucket (5') treated with the bactericide. The same measurement as above was carried out with regard to the sausage which passed through the sterilized bucket (5').

The results are shown in Table 15.

The data regarding the devices (2) to (5) and (2') to (5') were obtained with regard to a sterilized gauze which was used to swab a 30 cm×30 cm zone of each of these devices.

TABLE 15

| Sites inspected | | Standard plate count | Lactic acid bacteria | Coliform organisms |
|---|---|---|---|---|
| Conventional process | | | | |
| (1) | Surface of Vienna sausage in the clean room (cells for each sausage) | $2.5 \times 10^2$ | $1.8 \times 10^2$ | + |
| (2) | That portion of the drum cutter which contacted the sausage | $2.0 \times 10^2$ | $8.8 \times 10^2$ | + |
| (3) | Surface of the conveyor | $6.2 \times 10^3$ | $5.2 \times 10^3$ | + |
| (4) | Aligner | $7.2 \times 10^2$ | $5.3 \times 10^3$ | + |
| (5) | Bucket | $1.3 \times 10^4$ | $2.5 \times 10^4$ | + |
| (6) | The surface of the sausage which passed through the bucket (5) | $8.5 \times 10^4$ | $5.7 \times 10^4$ | + |
| Process of the invention | | | | |
| (1') | Vienna sausage (sprayed with a 10% solution of the bactericide) in the clean room | — | — | — |
| (2') | The product-contacting portion of the drum cutter sprayed with a 10% solution of the bactericide | — | — | — |
| (3') | Surface of the conveyor sprayed with a 10% solution of the bactericide | — | — | — |
| (4') | Aligner sprayed with a 10% solution of the bactericide | — | — | — |
| (5') | Bucket sprayed with a 10% solution of the bactericide | — | — | — |
| (6') | The surface of the sausage with passed | — | — | — |

TABLE 15-continued

| Sites inspected | Standard plate count | Lactic acid bacteria | Coliform organisms |
|---|---|---|---|
| through the bucket (5') | | | |

−: negative,
+: positive

EXAMPLE 8

Following experiment was conducted in order to demonstrate surprising technical advantage of a bactericide, or of a method for sterilization, of this invention.

1. Test material (1) Bacterial suspension

*Escherichia coli* (NIHJ-JC-2) was inoculated in a brain heart infusion broth (BHI), and cultivated at 37° C. for 24 hours. The culture broth was diluted to 1/10 with sterilized physiological saline. This *Escherichia coli* suspension was used as a sample suspension.

(2) Organic acids:

Lactic acid, acetic acid, citric acid, d-tartaric acid, gluconic acid, malic acid, ascorbic acid and phytic acid were used.

2. Test procedure

One (1) milliliter of the sample bacterial suspension was added to 9 ml of a sample chemical solution prepared in advance by adding physiological saline in such a manner as to have the respective concentrations of ethyl alcohol, one of said organic acids and phosphoric acid reaching 10/9 of given concentrations shown in Tables 16–23, immediately mixed together and then maintained at 20° C. After the lapse of contact time of 30 seconds, a loopful of this mixrure was inoculated into a fresh BHI broth and cultivated at 37° C. for 48 hours. Growth of the bacteria in the culture broth was observed with the unaided eye. When growth of bacteria was not observed, it was evaluated as (−) indicating that complete sterilization was possible, and when growth of bacteria was observed, it was evaluated as (+) indicating that sterilization was impossible. The concentrations of the chemical solutions required for complete sterilization were measured, respectively.

3. Test results

Test results were shown in following Tables 16–23:

TABLE 16

| Phosphoric acid | Lactic acid | Ethyl alcohol (%) | | | | | | | | | | | |
|---|---|---|---|---|---|---|---|---|---|---|---|---|---|
| (%) | (%) | 40 | 35 | 30 | 25 | 20 | 15 | 10 | 5 | 3 | 1 | 0.5 | 0 |
| 0 | 35 | − | − | − | − | − | − | − | − | − | − | − | − |
| | 30 | − | − | − | − | − | − | − | − | − | − | − | − |
| | 20 | − | − | − | − | − | − | − | − | + | + | + | + |
| | 10 | − | − | − | − | − | − | − | − | + | + | + | + |
| | 5 | − | − | − | − | − | − | − | + | + | + | + | + |
| | 1 | − | − | − | − | − | − | + | + | + | + | + | + |
| | 0.3 | − | − | − | − | + | + | + | + | + | + | + | + |
| | 0 | − | + | + | + | + | + | + | + | + | + | + | + |
| 0.03 | 35 | − | − | − | − | − | − | − | − | − | − | − | − |
| | 30 | − | − | − | − | − | − | − | − | − | − | − | + |
| | 20 | − | − | − | − | − | − | − | − | − | − | + | + |
| | 10 | − | − | − | − | − | − | − | − | − | − | + | + |
| | 5 | − | − | − | − | − | − | − | − | − | − | + | + |
| | 1 | − | − | − | − | − | − | − | − | − | − | + | + |
| | 0.3 | − | − | − | − | − | − | − | − | − | − | + | + |
| | 0 | − | + | + | + | + | + | + | + | + | + | + | + |
| 0.1 | 35 | − | − | − | − | − | − | − | − | − | − | − | − |
| | 30 | − | − | − | − | − | − | − | − | − | − | − | − |
| | 20 | − | − | − | − | − | − | − | − | − | − | + | + |
| | 10 | − | − | − | − | − | − | − | − | − | − | + | + |
| | 5 | − | − | − | − | − | − | − | − | − | − | + | + |
| | 1 | − | − | − | − | − | − | − | − | − | − | + | + |
| | 0.3 | − | − | − | − | − | − | − | − | − | − | + | + |
| | 0 | − | − | + | + | + | + | + | + | + | + | + | + |
| 0.5 | 35 | − | − | − | − | − | − | − | − | − | − | − | − |
| | 30 | − | − | − | − | − | − | − | − | − | − | − | − |
| | 20 | − | − | − | − | − | − | − | − | − | − | − | + |
| | 10 | − | − | − | − | − | − | − | − | − | − | + | + |
| | 5 | − | − | − | − | − | − | − | − | − | − | + | + |
| | 1 | − | − | − | − | − | − | − | − | − | − | + | + |
| | 0.3 | − | − | − | − | − | − | − | − | − | − | + | + |
| | 0 | − | − | + | + | + | + | + | + | + | + | + | + |
| 0.7 | 35 | − | − | − | − | − | − | − | − | − | − | − | − |
| | 30 | − | − | − | − | − | − | − | − | − | − | − | − |
| | 20 | − | − | − | − | − | − | − | − | − | − | + | + |
| | 10 | − | − | − | − | − | − | − | − | − | − | + | + |
| | 5 | − | − | − | − | − | − | − | − | − | − | + | + |
| | 1 | − | − | − | − | − | − | − | − | − | − | + | + |
| | 0.3 | − | − | − | − | − | − | − | − | − | − | + | + |
| | 0 | − | − | + | + | + | + | + | + | + | + | + | + |
| 1.0 | 35 | − | − | − | − | − | − | − | − | − | − | − | − |
| | 30 | − | − | − | − | − | − | − | − | − | − | − | + |
| | 20 | − | − | − | − | − | − | − | − | − | − | − | + |
| | 10 | − | − | − | − | − | − | − | − | − | − | + | + |
| | 5 | − | − | − | − | − | − | − | − | − | − | + | + |
| | 1 | − | − | − | − | − | − | − | − | − | − | + | + |
| | 0.3 | − | − | − | − | − | − | − | − | − | − | + | + |

TABLE 16-continued

| Phosphoric acid (%) | Lactic acid (%) | Ethyl alcohol (%) 40 | 35 | 30 | 25 | 20 | 15 | 10 | 5 | 3 | 1 | 0.5 | 0 |
|---|---|---|---|---|---|---|---|---|---|---|---|---|---|
| | 0 | − | − | − | − | − | + | + | + | + | + | + | + |

TABLE 17

| Phosphoric acid (%) | Acetic acid (%) | Ethyl alcohol (%) 40 | 35 | 30 | 25 | 20 | 15 | 10 | 5 | 3 | 1 | 0.5 | 0 |
|---|---|---|---|---|---|---|---|---|---|---|---|---|---|
| 0 | 35 | − | − | − | − | − | − | − | − | − | − | − | − |
| | 30 | − | − | − | − | − | − | − | − | − | − | − | + |
| | 20 | − | − | − | − | − | − | − | − | + | + | + | + |
| | 10 | − | − | − | − | − | − | − | − | + | + | + | + |
| | 5 | − | − | − | − | − | − | − | + | + | + | + | + |
| | 1 | − | − | − | − | − | − | + | + | + | + | + | + |
| | 0.3 | − | − | − | − | + | + | + | + | + | + | + | + |
| | 0 | − | + | + | + | + | + | + | + | + | + | + | + |
| 0.03 | 35 | − | − | − | − | − | − | − | − | − | − | − | − |
| | 30 | − | − | − | − | − | − | − | − | − | − | − | + |
| | 20 | − | − | − | − | − | − | − | − | − | − | + | + |
| | 10 | − | − | − | − | − | − | − | − | − | − | + | + |
| | 5 | − | − | − | − | − | − | − | − | − | − | + | + |
| | 1 | − | − | − | − | − | − | − | − | − | − | + | + |
| | 0.3 | − | − | − | − | − | − | − | − | + | + | + | + |
| | 0 | − | + | + | + | + | + | + | + | + | + | + | + |
| 0.1 | 35 | − | − | − | − | − | − | − | − | − | − | − | − |
| | 30 | − | − | − | − | − | − | − | − | − | − | − | − |
| | 20 | − | − | − | − | − | − | − | − | − | − | + | + |
| | 10 | − | − | − | − | − | − | − | − | − | − | + | + |
| | 5 | − | − | − | − | − | − | − | − | − | − | + | + |
| | 1 | − | − | − | − | − | − | − | − | − | − | + | + |
| | 0.3 | − | − | − | − | − | − | − | − | + | + | + | + |
| | 0 | − | − | + | + | + | + | + | + | + | + | + | + |
| 0.5 | 35 | − | − | − | − | − | − | − | − | − | − | − | − |
| | 30 | − | − | − | − | − | − | − | − | − | − | − | − |
| | 20 | − | − | − | − | − | − | − | − | − | − | − | + |
| | 10 | − | − | − | − | − | − | − | − | − | − | + | + |
| | 5 | − | − | − | − | − | − | − | − | − | − | + | + |
| | 1 | − | − | − | − | − | − | − | − | − | − | + | + |
| | 0.3 | − | − | − | − | − | − | − | − | − | + | + | + |
| | 0 | − | − | + | + | + | + | + | + | + | + | + | + |
| 0.7 | 35 | − | − | − | − | − | − | − | − | − | − | − | − |
| | 30 | − | − | − | − | − | − | − | − | − | − | − | − |
| | 20 | − | − | − | − | − | − | − | − | − | − | − | + |
| | 10 | − | − | − | − | − | − | − | − | − | − | + | + |
| | 5 | − | − | − | − | − | − | − | − | − | − | + | + |
| | 1 | − | − | − | − | − | − | − | − | − | − | + | + |
| | 0.3 | − | − | − | − | − | − | − | − | − | + | + | + |
| | 0 | − | − | + | + | + | + | + | + | + | + | + | + |
| 1.0 | 35 | − | − | − | − | − | − | − | − | − | − | − | − |
| | 30 | − | − | − | − | − | − | − | − | − | − | − | − |
| | 20 | − | − | − | − | − | − | − | − | − | − | − | + |
| | 10 | − | − | − | − | − | − | − | − | − | − | + | + |
| | 5 | − | − | − | − | − | − | − | − | − | − | + | + |
| | 1 | − | − | − | − | − | − | − | − | − | + | + | + |
| | 0.3 | − | − | − | − | − | − | − | − | − | + | + | + |
| | 0 | − | − | + | + | + | + | + | + | + | + | + | + |

TABLE 18

| Phosphoric acid (%) | Citric acid (%) | Ethyl alcohol (%) 40 | 35 | 30 | 25 | 20 | 15 | 10 | 5 | 3 | 1 | 0.5 | 0 |
|---|---|---|---|---|---|---|---|---|---|---|---|---|---|
| 0 | 35 | − | − | − | − | − | − | − | − | − | − | − | − |
| | 30 | − | − | − | − | − | − | − | − | − | − | − | + |
| | 20 | − | − | − | + | + | + | + | + | + | + | + | + |
| | 10 | − | − | − | + | + | + | + | + | + | + | + | + |
| | 5 | − | − | + | + | + | + | + | + | + | + | + | + |
| | 1 | − | + | + | + | + | + | + | + | + | + | + | + |
| | 0.3 | − | + | + | + | + | + | + | + | + | + | + | + |
| | 0 | − | + | + | + | + | + | + | + | + | + | + | + |
| 0.03 | 35 | − | − | − | − | − | − | − | − | − | − | − | − |
| | 30 | − | − | − | − | − | − | − | − | − | − | − | + |
| | 20 | − | − | − | − | − | − | − | − | − | − | + | + |

TABLE 18-continued

| Phosphoric acid (%) | Citric acid (%) | Ethyl alcohol (%) 40 | 35 | 30 | 25 | 20 | 15 | 10 | 5 | 3 | 1 | 0.5 | 0 |
|---|---|---|---|---|---|---|---|---|---|---|---|---|---|
| | 10 | − | − | − | − | − | − | − | − | − | − | + | + |
| | 5 | − | − | − | + | + | + | + | + | + | + | + | + |
| | 1 | − | + | + | + | + | + | + | + | + | + | + | + |
| | 0.3 | − | + | + | + | + | + | + | + | + | + | + | + |
| | 0 | − | + | + | + | + | + | + | + | + | + | + | + |
| 0.1 | 35 | − | − | − | − | − | − | − | − | − | − | − | − |
| | 30 | − | − | − | − | − | − | − | − | − | − | − | + |
| | 20 | − | − | − | − | − | − | − | − | − | − | + | + |
| | 10 | − | − | − | − | − | − | − | − | − | − | + | + |
| | 5 | − | − | − | − | − | − | − | + | + | + | + | + |
| | 1 | − | − | − | + | + | + | + | + | + | + | + | + |
| | 0.3 | − | + | + | + | + | + | + | + | + | + | + | + |
| | 0 | − | + | + | + | + | + | + | + | + | + | + | + |
| 0.5 | 35 | − | − | − | − | − | − | − | − | − | − | − | − |
| | 30 | − | − | − | − | − | − | − | − | − | − | − | + |
| | 20 | − | − | − | − | − | − | − | − | − | − | + | + |
| | 10 | − | − | − | − | − | − | − | − | − | − | + | + |
| | 5 | − | − | − | − | − | − | − | − | − | + | + | + |
| | 1 | − | − | − | − | − | − | − | + | + | + | + | + |
| | 0.3 | − | − | + | + | + | + | + | + | + | + | + | + |
| | 0 | − | + | + | + | + | + | + | + | + | + | + | + |
| 0.7 | 35 | − | − | − | − | − | − | − | − | − | − | − | − |
| | 30 | − | − | − | − | − | − | − | − | − | − | − | + |
| | 20 | − | − | − | − | − | − | − | − | − | − | + | + |
| | 10 | − | − | − | − | − | − | − | − | − | − | + | + |
| | 5 | − | − | − | − | − | − | − | − | − | − | + | + |
| | 1 | − | − | − | − | − | − | − | − | + | + | + | + |
| | 0.3 | − | − | + | + | + | + | + | + | + | + | + | + |
| | 0 | − | + | + | + | + | + | + | + | + | + | + | + |
| 1.0 | 35 | − | − | − | − | − | − | − | − | − | − | − | − |
| | 30 | − | − | − | − | − | − | − | − | − | − | − | + |
| | 20 | − | − | − | − | − | − | − | − | − | − | + | + |
| | 10 | − | − | − | − | − | − | − | − | − | − | + | + |
| | 5 | − | − | − | − | − | − | − | − | − | − | + | + |
| | 1 | − | − | − | − | − | − | − | − | + | + | + | + |
| | 0.3 | − | − | − | − | + | + | + | + | + | + | + | + |
| | 0 | − | − | + | + | + | + | + | + | + | + | + | + |

TABLE 19

| Phosphoric acid (%) | d-Tartaric acid (%) | Ethyl alcohol (%) 40 | 35 | 30 | 25 | 20 | 15 | 10 | 5 | 3 | 1 | 0.5 | 0 |
|---|---|---|---|---|---|---|---|---|---|---|---|---|---|
| 0 | 35 | − | − | − | − | − | − | − | − | − | − | − | − |
| | 30 | − | − | − | − | − | − | − | − | − | − | − | + |
| | 20 | − | − | − | + | + | + | + | + | + | + | + | + |
| | 10 | − | − | − | + | + | + | + | + | + | + | + | + |
| | 5 | − | − | + | + | + | + | + | + | + | + | + | + |
| | 1 | − | + | + | + | + | + | + | + | + | + | + | + |
| | 0.3 | − | + | + | + | + | + | + | + | + | + | + | + |
| | 0 | − | + | + | + | + | + | + | + | + | + | + | + |
| 0.03 | 35 | − | − | − | − | − | − | − | − | − | − | − | − |
| | 30 | − | − | − | − | − | − | − | − | − | − | − | + |
| | 20 | − | − | − | − | − | − | − | − | − | − | + | + |
| | 10 | − | − | − | − | − | − | − | − | − | − | + | + |
| | 5 | − | − | − | + | + | + | + | + | + | + | + | + |
| | 1 | − | + | + | + | + | + | + | + | + | + | + | + |
| | 0.3 | − | + | + | + | + | + | + | + | + | + | + | + |
| | 0 | − | + | + | + | + | + | + | + | + | + | + | + |
| 0.1 | 35 | − | − | − | − | − | − | − | − | − | − | − | − |
| | 30 | − | − | − | − | − | − | − | − | − | − | − | + |
| | 20 | − | − | − | − | − | − | − | − | − | − | + | + |
| | 10 | − | − | − | − | − | − | − | − | − | − | + | + |
| | 5 | − | − | − | − | − | − | − | + | + | + | + | + |
| | 1 | − | − | + | + | + | + | + | + | + | + | + | + |
| | 0.3 | − | + | + | + | + | + | + | + | + | + | + | + |
| | 0 | − | + | + | + | + | + | + | + | + | + | + | + |
| 0.5 | 35 | − | − | − | − | − | − | − | − | − | − | − | − |
| | 30 | − | − | − | − | − | − | − | − | − | − | − | + |
| | 20 | − | − | − | − | − | − | − | − | − | − | + | + |
| | 10 | − | − | − | − | − | − | − | − | − | − | + | + |
| | 5 | − | − | − | − | − | − | − | − | − | − | + | + |
| | 1 | − | − | − | − | − | − | − | + | + | + | + | + |
| | 0.3 | − | − | + | + | + | + | + | + | + | + | + | + |

TABLE 19-continued

| Phosphoric acid (%) | d-Tartaric acid (%) | Ethyl alcohol (%) 40 | 35 | 30 | 25 | 20 | 15 | 10 | 5 | 3 | 1 | 0.5 | 0 |
|---|---|---|---|---|---|---|---|---|---|---|---|---|---|
| | 0 | − | + | + | + | + | + | + | + | + | + | + | + |
| 0.7 | 35 | − | − | − | − | − | − | − | − | − | − | − | − |
| | 30 | − | − | − | − | − | − | − | − | − | − | − | + |
| | 20 | − | − | − | − | − | − | − | − | − | − | + | + |
| | 10 | − | − | − | − | − | − | − | − | − | − | + | + |
| | 5 | − | − | − | − | − | − | − | − | − | − | + | + |
| | 1 | − | − | − | − | − | − | − | − | + | + | + | + |
| | 0.3 | − | − | + | + | + | + | + | + | + | + | + | + |
| | 0 | − | + | + | + | + | + | + | + | + | + | + | + |
| 1.0 | 35 | − | − | − | − | − | − | − | − | − | − | − | − |
| | 30 | − | − | − | − | − | − | − | − | − | − | − | + |
| | 20 | − | − | − | − | − | − | − | − | − | − | + | + |
| | 10 | − | − | − | − | − | − | − | − | − | − | + | + |
| | 5 | − | − | − | − | − | − | − | − | − | − | + | + |
| | 1 | − | − | − | − | − | − | − | − | + | + | + | + |
| | 0.3 | − | − | − | − | + | + | + | + | + | + | + | + |
| | 0 | − | − | + | + | + | + | + | + | + | + | + | + |

TABLE 20

| Phosphoric acid (%) | Gluconic acid (%) | Ethyl alcohol (%) 40 | 35 | 30 | 25 | 20 | 15 | 10 | 5 | 3 | 1 | 0.5 | 0 |
|---|---|---|---|---|---|---|---|---|---|---|---|---|---|
| 0 | 35 | − | − | − | − | − | − | − | − | − | − | − | − |
| | 30 | − | − | − | − | − | − | − | − | − | − | − | + |
| | 20 | − | − | − | + | + | + | + | + | + | + | + | + |
| | 10 | − | − | − | + | + | + | + | + | + | + | + | + |
| | 5 | − | − | + | + | + | + | + | + | + | + | + | + |
| | 1 | − | + | + | + | + | + | + | + | + | + | + | + |
| | 0.3 | − | + | + | + | + | + | + | + | + | + | + | + |
| | 0 | − | + | + | + | + | + | + | + | + | + | + | + |
| 0.03 | 35 | − | − | − | − | − | − | − | − | − | − | − | − |
| | 30 | − | − | − | − | − | − | − | − | − | − | − | + |
| | 20 | − | − | − | − | − | − | − | − | − | − | + | + |
| | 10 | − | − | − | − | − | − | − | − | − | − | + | + |
| | 5 | − | − | − | + | + | + | + | + | + | + | + | + |
| | 1 | − | + | + | + | + | + | + | + | + | + | + | + |
| | 0.3 | − | + | + | + | + | + | + | + | + | + | + | + |
| | 0 | − | + | + | + | + | + | + | + | + | + | + | + |
| 0.1 | 35 | − | − | − | − | − | − | − | − | − | − | − | − |
| | 30 | − | − | − | − | − | − | − | − | − | − | − | + |
| | 20 | − | − | − | − | − | − | − | − | − | − | + | + |
| | 10 | − | − | − | − | − | − | − | − | − | − | + | + |
| | 5 | − | − | − | − | − | − | − | + | + | + | + | + |
| | 1 | − | − | + | + | + | + | + | + | + | + | + | + |
| | 0.3 | − | + | + | + | + | + | + | + | + | + | + | + |
| | 0 | − | + | + | + | + | + | + | + | + | + | + | + |
| 0.5 | 35 | − | − | − | − | − | − | − | − | − | − | − | − |
| | 30 | − | − | − | − | − | − | − | − | − | − | − | + |
| | 20 | − | − | − | − | − | − | − | − | − | − | + | + |
| | 10 | − | − | − | − | − | − | − | − | − | − | + | + |
| | 5 | − | − | − | − | − | − | − | − | − | − | + | + |
| | 1 | − | − | − | − | − | − | − | + | + | + | + | + |
| | 0.3 | − | − | + | + | + | + | + | + | + | + | + | + |
| | 0 | − | + | + | + | + | + | + | + | + | + | + | + |
| 0.7 | 35 | − | − | − | − | − | − | − | − | − | − | − | − |
| | 30 | − | − | − | − | − | − | − | − | − | − | − | + |
| | 20 | − | − | − | − | − | − | − | − | − | − | + | + |
| | 10 | − | − | − | − | − | − | − | − | − | − | + | + |
| | 5 | − | − | − | − | − | − | − | − | − | − | + | + |
| | 1 | − | − | − | − | − | − | − | − | + | + | + | + |
| | 0.3 | − | − | + | + | + | + | + | + | + | + | + | + |
| | 0 | − | + | + | + | + | + | + | + | + | + | + | + |
| 1.0 | 35 | − | − | − | − | − | − | − | − | − | − | − | − |
| | 30 | − | − | − | − | − | − | − | − | − | − | − | + |
| | 20 | − | − | − | − | − | − | − | − | − | − | + | + |
| | 10 | − | − | − | − | − | − | − | − | − | − | + | + |
| | 5 | − | − | − | − | − | − | − | − | − | − | + | + |
| | 1 | − | − | − | − | − | − | − | − | + | + | + | + |
| | 0.3 | − | − | − | − | + | + | + | + | + | + | + | + |
| | 0 | − | − | + | + | + | + | + | + | + | + | + | + |

TABLE 21

| Phosphoric acid | Malic acid | Ethyl alcohol (%) | | | | | | | | | | | |
|---|---|---|---|---|---|---|---|---|---|---|---|---|---|
| (%) | (%) | 40 | 35 | 30 | 25 | 20 | 15 | 10 | 5 | 3 | 1 | 0.5 | 0 |
| 0 | 35 | − | − | − | − | − | − | − | − | − | − | − | − |
| | 30 | − | − | − | − | − | − | − | − | − | − | − | + |
| | 20 | − | − | − | − | − | + | + | + | + | + | + | + |
| | 10 | − | − | − | − | − | + | + | + | + | + | + | + |
| | 5 | − | − | − | − | + | + | + | + | + | + | + | + |
| | 1 | − | − | − | + | + | + | + | + | + | + | + | + |
| | 0.3 | − | − | − | + | + | + | + | + | + | + | + | + |
| | 0 | − | + | + | + | + | + | + | + | + | + | + | + |
| 0.03 | 35 | − | − | − | − | − | − | − | − | − | − | − | − |
| | 30 | − | − | − | − | − | − | − | − | − | − | − | + |
| | 20 | − | − | − | − | − | − | − | − | − | − | + | + |
| | 10 | − | − | − | − | − | − | − | − | − | − | + | + |
| | 5 | − | − | − | − | − | − | − | − | − | − | + | + |
| | 1 | − | − | − | − | − | − | − | + | + | + | + | + |
| | 0.3 | − | − | − | − | − | − | + | + | + | + | + | + |
| | 0 | − | + | + | + | + | + | + | + | + | + | + | + |
| 0.1 | 35 | − | − | − | − | − | − | − | − | − | − | − | − |
| | 30 | − | − | − | − | − | − | − | − | − | − | − | − |
| | 20 | − | − | − | − | − | − | − | − | − | − | + | + |
| | 10 | − | − | − | − | − | − | − | − | − | − | + | + |
| | 5 | − | − | − | − | − | − | − | − | − | − | + | + |
| | 1 | − | − | − | − | − | − | − | − | + | + | + | + |
| | 0.3 | − | − | − | − | − | − | − | + | + | + | + | + |
| | 0 | − | − | + | + | + | + | + | + | + | + | + | + |
| 0.5 | 35 | − | − | − | − | − | − | − | − | − | − | − | − |
| | 30 | − | − | − | − | − | − | − | − | − | − | − | − |
| | 20 | − | − | − | − | − | − | − | − | − | − | − | + |
| | 10 | − | − | − | − | − | − | − | − | − | − | + | + |
| | 5 | − | − | − | − | − | − | − | − | − | − | + | + |
| | 1 | − | − | − | − | − | − | − | − | − | + | + | + |
| | 0.3 | − | − | − | − | − | − | − | + | + | + | + | + |
| | 0 | − | − | + | + | + | + | + | + | + | + | + | + |
| 0.7 | 35 | − | − | − | − | − | − | − | − | − | − | − | − |
| | 30 | − | − | − | − | − | − | − | − | − | − | − | − |
| | 20 | − | − | − | − | − | − | − | − | − | − | − | + |
| | 10 | − | − | − | − | − | − | − | − | − | − | + | + |
| | 5 | − | − | − | − | − | − | − | − | − | − | + | + |
| | 1 | − | − | − | − | − | − | − | − | − | + | + | + |
| | 0.3 | − | − | − | − | − | − | − | + | + | + | + | + |
| | 0 | − | − | + | + | + | + | + | + | + | + | + | + |
| 1.0 | 35 | − | − | − | − | − | − | − | − | − | − | − | − |
| | 30 | − | − | − | − | − | − | − | − | − | − | − | − |
| | 20 | − | − | − | − | − | − | − | − | − | − | − | + |
| | 10 | − | − | − | − | − | − | − | − | − | − | + | + |
| | 5 | − | − | − | − | − | − | − | − | − | − | + | + |
| | 1 | − | − | − | − | − | − | − | − | − | + | + | + |
| | 0.3 | − | − | − | − | − | − | − | − | + | + | + | + |
| | 0 | − | − | + | + | + | + | + | + | + | + | + | + |

TABLE 22

| Phosphoric acid | Ascorbic acid | Ethyl alcohol (%) | | | | | | | | | | | |
|---|---|---|---|---|---|---|---|---|---|---|---|---|---|
| (%) | (%) | 40 | 35 | 30 | 25 | 20 | 15 | 10 | 5 | 3 | 1 | 0.5 | 0 |
| 0 | 35 | − | − | − | − | − | − | − | − | − | − | − | − |
| | 30 | − | − | − | − | − | − | − | − | − | − | − | + |
| | 20 | − | − | − | − | − | + | + | + | + | + | + | + |
| | 10 | − | − | − | − | − | + | + | + | + | + | + | + |
| | 5 | − | − | − | − | + | + | + | + | + | + | + | + |
| | 1 | − | − | − | + | + | + | + | + | + | + | + | + |
| | 0.3 | − | − | − | + | + | + | + | + | + | + | + | + |
| | 0 | − | + | + | + | + | + | + | + | + | + | + | + |
| 0.03 | 35 | − | − | − | − | − | − | − | − | − | − | − | − |
| | 30 | − | − | − | − | − | − | − | − | − | − | − | + |
| | 20 | − | − | − | − | − | − | − | − | − | − | + | + |
| | 10 | − | − | − | − | − | − | − | − | − | − | + | + |
| | 5 | − | − | − | − | − | − | − | − | − | − | + | + |
| | 1 | − | − | − | − | − | − | − | + | + | + | + | + |
| | 0.3 | − | − | − | − | − | − | − | + | + | + | + | + |
| | 0 | − | + | + | + | + | + | + | + | + | + | + | + |
| 0.1 | 35 | − | − | − | − | − | − | − | − | − | − | − | − |
| | 30 | − | − | − | − | − | − | − | − | − | − | − | − |
| | 20 | − | − | − | − | − | − | − | − | − | − | + | + |
| | 10 | − | − | − | − | − | − | − | − | − | − | + | + |

TABLE 22-continued

| Phosphoric acid (%) | Ascorbic acid (%) | Ethyl alcohol (%) 40 | 35 | 30 | 25 | 20 | 15 | 10 | 5 | 3 | 1 | 0.5 | 0 |
|---|---|---|---|---|---|---|---|---|---|---|---|---|---|
| | 5 | − | − | − | − | − | − | − | − | − | − | + | + |
| | 1 | − | − | − | − | − | − | − | − | + | + | + | + |
| | 0.3 | − | − | − | − | − | − | − | + | + | + | + | + |
| | 0 | − | − | + | + | + | + | + | + | + | + | + | + |
| 0.5 | 35 | − | − | − | − | − | − | − | − | − | − | − | − |
| | 30 | − | − | − | − | − | − | − | − | − | − | − | − |
| | 20 | − | − | − | − | − | − | − | − | − | − | − | + |
| | 10 | − | − | − | − | − | − | − | − | − | − | + | + |
| | 5 | − | − | − | − | − | − | − | − | − | − | + | + |
| | 1 | − | − | − | − | − | − | − | − | − | + | + | + |
| | 0.3 | − | − | − | − | − | − | − | + | + | + | + | + |
| | 0 | − | − | + | + | + | + | + | + | + | + | + | + |
| 0.7 | 35 | − | − | − | − | − | − | − | − | − | − | − | − |
| | 30 | − | − | − | − | − | − | − | − | − | − | − | − |
| | 20 | − | − | − | − | − | − | − | − | − | − | − | + |
| | 10 | − | − | − | − | − | − | − | − | − | − | + | + |
| | 5 | − | − | − | − | − | − | − | − | − | − | + | + |
| | 1 | − | − | − | − | − | − | − | − | − | + | + | + |
| | 0.3 | − | − | − | − | − | − | − | + | + | + | + | + |
| | 0 | − | − | + | + | + | + | + | + | + | + | + | + |
| 1.0 | 35 | − | − | − | − | − | − | − | − | − | − | − | − |
| | 30 | − | − | − | − | − | − | − | − | − | − | − | − |
| | 20 | − | − | − | − | − | − | − | − | − | − | − | + |
| | 10 | − | − | − | − | − | − | − | − | − | − | + | + |
| | 5 | − | − | − | − | − | − | − | − | − | − | + | + |
| | 1 | − | − | − | − | − | − | − | − | − | + | + | + |
| | 0.3 | − | − | − | − | − | − | − | − | + | + | + | + |
| | 0 | − | − | + | + | + | + | + | + | + | + | + | + |

TABLE 23

| Phosphoric acid (%) | Phytic acid (%) | Ethyl alcohol (%) 40 | 35 | 30 | 25 | 20 | 15 | 10 | 5 | 3 | 1 | 0.5 | 0 |
|---|---|---|---|---|---|---|---|---|---|---|---|---|---|
| 0 | 35 | − | − | − | − | − | − | − | − | − | − | − | − |
| | 30 | − | − | − | − | − | − | − | − | − | − | − | − |
| | 20 | − | − | − | − | − | − | − | − | + | + | + | + |
| | 10 | − | − | − | − | − | − | + | + | + | + | + | + |
| | 5 | − | − | − | − | − | − | + | + | + | + | + | + |
| | 1 | − | − | − | − | − | − | + | + | + | + | + | + |
| | 0.3 | − | − | − | − | + | + | + | + | + | + | + | + |
| | 0 | − | + | + | + | + | + | + | + | + | + | + | + |
| 0.03 | 35 | − | − | − | − | − | − | − | − | − | − | − | − |
| | 30 | − | − | − | − | − | − | − | − | − | − | − | + |
| | 20 | − | − | − | − | − | − | − | − | − | − | + | + |
| | 10 | − | − | − | − | − | − | − | − | − | − | + | + |
| | 5 | − | − | − | − | − | − | − | − | − | − | + | + |
| | 1 | − | − | − | − | − | − | − | − | − | − | + | + |
| | 0.3 | − | − | − | − | − | − | − | + | + | + | + | + |
| | 0 | − | + | + | + | + | + | + | + | + | + | + | + |
| 0.1 | 35 | − | − | − | − | − | − | − | − | − | − | − | − |
| | 30 | − | − | − | − | − | − | − | − | − | − | − | − |
| | 20 | − | − | − | − | − | − | − | − | − | − | + | + |
| | 10 | − | − | − | − | − | − | − | − | − | − | + | + |
| | 5 | − | − | − | − | − | − | − | − | − | − | + | + |
| | 1 | − | − | − | − | − | − | − | − | − | − | + | + |
| | 0.3 | − | − | − | − | − | − | − | − | + | + | + | + |
| | 0 | − | + | + | + | + | + | + | + | + | + | + | + |
| 0.5 | 35 | − | − | − | − | − | − | − | − | − | − | − | − |
| | 30 | − | − | − | − | − | − | − | − | − | − | − | − |
| | 20 | − | − | − | − | − | − | − | − | − | − | − | + |
| | 10 | − | − | − | − | − | − | − | − | − | − | + | + |
| | 5 | − | − | − | − | − | − | − | − | − | − | + | + |
| | 1 | − | − | − | − | − | − | − | − | − | − | + | + |
| | 0.3 | − | − | − | − | − | − | − | − | − | + | + | + |
| | 0 | − | − | + | + | + | + | + | + | + | + | + | + |
| 0.7 | 35 | − | − | − | − | − | − | − | − | − | − | − | − |
| | 30 | − | − | − | − | − | − | − | − | − | − | − | − |
| | 20 | − | − | − | − | − | − | − | − | − | − | − | + |
| | 10 | − | − | − | − | − | − | − | − | − | − | + | + |
| | 5 | − | − | − | − | − | − | − | − | − | − | + | + |
| | 1 | − | − | − | − | − | − | − | − | − | − | + | + |
| | 0.3 | − | − | − | − | − | − | − | − | − | + | + | + |
| | 0 | − | − | + | + | + | + | + | + | + | + | + | + |

TABLE 23-continued

| Phosphoric acid (%) | Phytic acid (%) | Ethyl alcohol (%) 40 | 35 | 30 | 25 | 20 | 15 | 10 | 5 | 3 | 1 | 0.5 | 0 |
|---|---|---|---|---|---|---|---|---|---|---|---|---|---|
| 1.0 | 35 | − | − | − | − | − | − | − | − | − | − | − | − |
| | 30 | − | − | − | − | − | − | − | − | − | − | − | − |
| | 20 | − | − | − | − | − | − | − | − | − | − | − | + |
| | 10 | − | − | − | − | − | − | − | − | − | − | + | + |
| | 5 | − | − | − | − | − | − | − | − | − | − | + | + |
| | 1 | − | − | − | − | − | − | − | − | − | − | + | + |
| | 0.3 | − | − | − | − | − | − | − | − | − | + | + | + |
| | 0 | − | − | + | + | + | + | + | + | + | + | + | + |

4. Observations and conclusions

It is noted from data given in Tables 16–23 above that the joint use of three components of ethyl alcohol, a specified organic acid (lactic acid, acetic acid, citric acid, d-tartaric acid, gluconic acid, malic acid, ascorbic acid or phytic acid) and phosphoric acid brings about remarkable synergetic sterilizing effect which is not produced by the single use of respective components or joint use of the two of these respective components. Thus, it is confirmed that sterilization is performed within 30 seconds in the case of joint use of three components of ethyl alcohol in a concentration of 14–1% (W/V), a specified organic acid 13.0–0.3% (W/V) and phosphoric acid 0.7–0.03% (W/V) according to this invention.

What we claimed is:

1. A liquid bactericide for foods and food processing machines or utensils, said bactericide consisting essentially of a synergistically effective amount of the active ingredients, 98.0 to 2.3% (W/V) of ethyl alcohol, 1.0 to 96.7% (W/V) of an organic acid selected from the group consisting of lactic acid, acetic acid, citric acid, tartaric acid, gluconic acid, malic acid, ascorbic acid and phytic acid and 1.0 to 96.7% (W/V) of phosphoric acid; said bactericide being capable of sterilizing within 30 seconds when used in an aqueous solution, such that the concentration of active ingredients in solution consists of 14 to 1% (W/V) of ethyl alcohol, 13.0 to 0.3% (W/V) of said organic acid and 0.7 to 0.03% (W/V) of phosphoric acid.

2. The bactericide of claim 1 wherein the organic acid is lactic acid, acetic acid, citric acid, malic acid or phytic acid.

3. The bactericide of claim 1 wherein the organic acid is lactic acid, acetic acid or phytic acid.

4. The bactericide of claim 1 wherein the organic acid is lactic acid.

5. The bactericide of claim 1, wherein the liquid bactericide is in the form of an aqueous solution having a pH of not more than 4.0.

6. A liquid bactericide for foods and food processing machines or utensils consisting essentially of a synergistically effective amount of an aqueous solution of 18.6 to 1% (W/V) of ethyl alcohol, 31 to 0.3% (W/V) of an organic acid selected from the group consisting of lactic acid, acetic acid, citric acid, tartaric acid, gluconic acid, malic acid, ascorbic acid and phytic acid and 0.7 to 0.05% (W/V) of phosphoric acid, said solution having a pH of not more than 4.0.

7. The bactericide of claim 6 wherein the aqueous solution consists essentially of 14 to 1% (W/V) of ethyl alcohol, 13.0 to 0.3% (W/V) of the organic acid and 0.7 to 0.03% (W/V) of phosphoric acid.

* * * * *